(12) United States Patent
Srivastava et al.

(10) Patent No.: US 11,357,766 B2
(45) Date of Patent: Jun. 14, 2022

(54) COMPOSITIONS AND METHODS FOR TREATING CANCER

(71) Applicant: Texas Tech University System, Lubbock, TX (US)

(72) Inventors: Sanjay K. Srivastava, Abilene, TX (US); Sharavan Ramachandran, Abilene, TX (US)

(73) Assignee: Texas Tech University System, Lubbock, TX (US)

( * ) Notice: Subject to any disclaimer, the term of this patent is extended or adjusted under 35 U.S.C. 154(b) by 22 days.

(21) Appl. No.: 16/762,525

(22) PCT Filed: Nov. 13, 2018

(86) PCT No.: PCT/US2018/060763
§ 371 (c)(1),
(2) Date: May 8, 2020

(87) PCT Pub. No.: WO2019/094940
PCT Pub. Date: May 16, 2019

(65) Prior Publication Data
US 2020/0268732 A1 Aug. 27, 2020

Related U.S. Application Data

(60) Provisional application No. 62/585,080, filed on Nov. 13, 2017.

(51) Int. Cl.
*A61K 31/4468* (2006.01)
*A61P 35/00* (2006.01)

(52) U.S. Cl.
CPC .......... *A61K 31/4468* (2013.01); *A61P 35/00* (2018.01)

(58) Field of Classification Search
CPC ................................................ A61K 31/4468
USPC ....................................................... 514/329
See application file for complete search history.

(56) References Cited

U.S. PATENT DOCUMENTS

| | | | |
|---|---|---|---|
| 7,713,995 B2 * | 5/2010 | Weiner .................... | A61P 25/16 514/310 |
| 9,717,724 B2 | 8/2017 | Bayever et al. | |
| 9,758,786 B2 | 9/2017 | Trieu | |

FOREIGN PATENT DOCUMENTS

WO 2014/018563 A2 1/2014

OTHER PUBLICATIONS

Nuplazid prescribing information (2016) Acadia, San Diego, CA.*
Adikrisna, R. et al. "Identification of pancreatic cancer stem cells and selective toxicity of chemotherapeutic agents." Gastroenterology. 2012;143(1):234-45 e7.
Cruz, "Pimavanserin (Nuplazid)—A Treatment for Hallucinations and Delusions Associated With Parkinson's Disease", Drug Forecast (2017), vol. 42, No. 6, pp. 368-371.
Fatima et al., "5-Hydroxytryptamine promotes hepatocellular carcinoma proliferation by influencing β-catenin", Molecular Oncology (2016), vol. 10, pp. 195-212.
Gooz M et al. "5-HT2A receptor induces ERK phosphorylation and proliferation through ADAIM-17 tumor necrosis factor-alpha-converting enzyme (TACE) activation and heparin-bound epidermal growth factor-like growth factor (HBEGF) shedding in mesangial cells." The Journal of biological chemistry. 2006;281(30):121004-12.
Inaguma, S et al. "GLI1 interferes with the DNA mismatch repair system in pancreatic cancer through BHLHE41-mediated suppression of IMLH1." Cancer research. 2013;73(24):7313-23.
International Search Report, PCT/US2018/060763 [ISA/AU] dated Jan. 18, 2019.
Kasai, K "GLI1, a master regulator of the hallmark of pancreatic cancer." Pathology international. 2016;66(12):1653-60. [abstract].
Marechal, R et al. "Sonic hedgehog and Gli 1 expression predict outcome in resected pancreatic adenocarcinoma." Clinical cancer research : an official journal of the American Association for Cancer Research. 2015;21(5):1215-24.
Menezes et al., "Prevention of Photocarcinogenesis by Agonists of 5-HT1A and Antagonists of 5-HT2A Receptors", Molecular Neurobiology (2016), vol. 53, No. 2,pp. 1145-1164 [abstract].
Onishi, H et al. "Hedgehog signaling pathway as a new therapeutic target in pancreatic cancer." World journal of gastroenterology. 2014;20(9):2335-42.
Peters et al., "Dopamine and serotonin regulate tumor behavior by affecting angiogenesis", Drug Resistance Updates (2014), vol. 17, No. 4-6, pp. 96-104 [abstract].
Ramachandran et al., "Novel anti-psychotic drug for pancreatic cancer treatment"[abstract]. In: Proceedings of the American Association for Cancer Research Annual Meeting 2018; Apr. 14-18, 2018; Chicago, IL. Philadelphia (PA) AACR; Cancer Res(2018), vol. 78, No. 13 Suppl, Abstract LB-047.
Ranjan, A et al. "Penfluridol induces endoplasmic reticulum stress leading to autophagy in pancreatic cancer." Tumour biology : the journal of the International Society for Oncodevelopmental Biology and Medicine. 2017;39 (6):1010428317705517.
Ranjan, A et al. "Penfluridol suppresses glioblastoma tumor growth by Akt-mediated inhibition of GLI1." Oncotarget 2017;8(20):32960-76.
Ranjan, A et al. "Penfluridol suppresses pancreatic tumor growth by autophagy-mediated apoptosis." Scientific reports. 2016;6:26165.
Ranjan, A et al. "Penfluridol: An Antipsychotic Agent Suppresses Metastatic Tumor Growth in Triple-Negative Breast Cancer by Inhibiting Integrin Signaling Axis." Cancer research. 2016;76(4):877-90.
Ranjan, A et al. "Immune consequences of penfluridol treatment associated with inhibition of glioblastoma tumor growth." Oncotarget. 2017;8(29):47632-41.

(Continued)

*Primary Examiner* — Taofiq A Solola
(74) *Attorney, Agent, or Firm* — Edwin S. Flores; Daniel J. Chalker; Chalker Flores, LLP

(57) ABSTRACT

The present invention includes composition and methods for treating cancers comprising administering to a subject a pharmaceutical composition comprising Pimavanserin or derivatives thereof in an amount sufficient to treat the reproductive cancer in the subject and a pharmaceutically acceptable carrier.

9 Claims, 11 Drawing Sheets

(56) References Cited

OTHER PUBLICATIONS

Soll et al., "Expression of Serotonin Receptors in Human Hepatocellular Cancer",Clinical Cancer Research (2012), vol. 18, No. 21, pp. 5902-5910.
Soil et al., "Serotonin Promotes Tumor Growth in Human Hepatocellular Cancer",Hepatology (2010), vol. 51, pp. 1244-1254.
Sonier B et al. "The 5-HT2A serotoninergic receptor is expressed in the MCF-7 human breast cancer cell line and reveals a mitogenic effect of serotonin." Biochemical and biophysical research communications. 2006;343(4):1053-9.
Srivastava SK et al. "Cell cycle arrest, apoptosis induction and inhibition of nuclear factor kappa B activation in anti-proliferative activity of benzyl isothiocyanate against human pancreatic cancer cells." Carcinogenesis. 2004;25 (9):1701-9.
Subramani, R et al. "Gedunin inhibits pancreatic cancer by altering sonic hedgehog signaling pathway." Oncotarget. 2017;8(7):10891-904.
Wiklund, ED et al. "Cytotoxic effects of antipsychotic drugs implicate cholesterol homeostasis as a novel chemotherapeutic target." International journal of cancer. 2010;126(1):28-40.
Yuan K et al. "Calmodulin antagonists promote TRA-8 therapy of resistant pancreatic cancer." Oncotarget. 2015;6 (28):125308-19.
Extended European Search Report, EP 18876271.0 dated Jul. 12, 2021.

\* cited by examiner

Pancreatic cancer
FIG.1A AsPC1
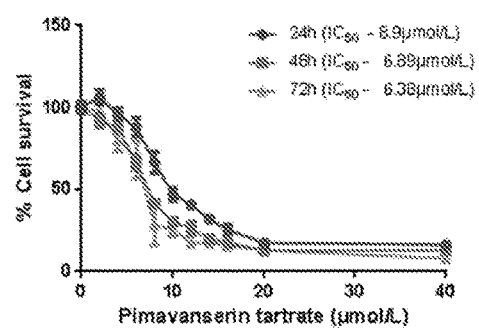
FIG.1B BxPC3
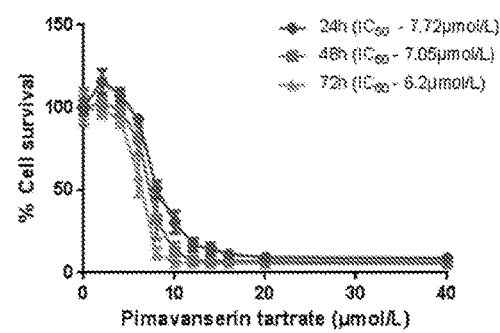
FIG.1C PANC1
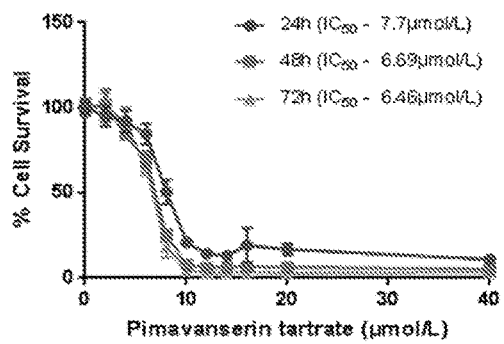
FIG.1D MIAPaCa2
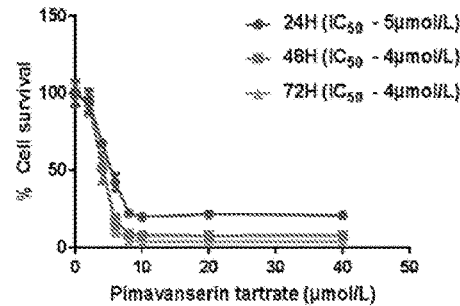
FIG.1E PO2
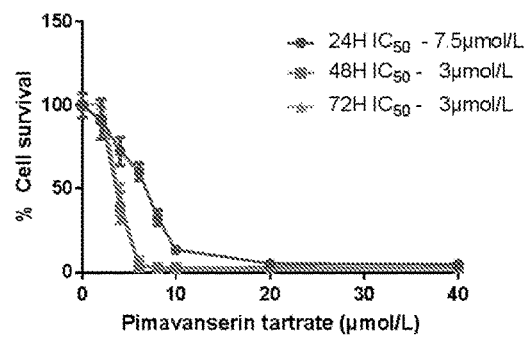

Melanoma
FIG.1F A375 VR
FIG.1G SKMEL28
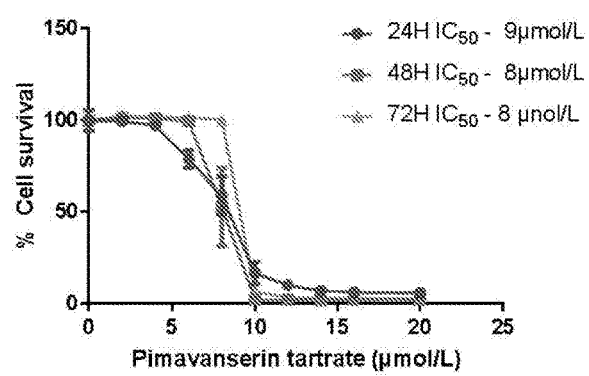
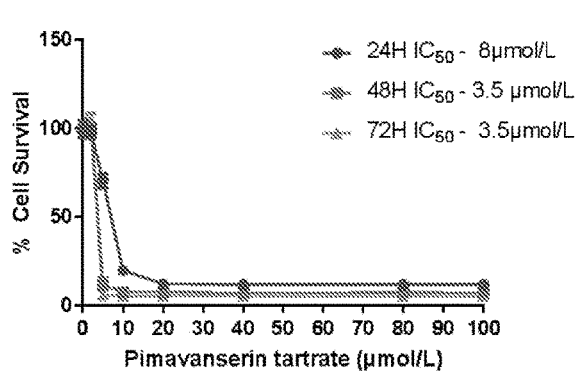
Colon cancer
FIG.1H HCT-116
Breast cancer
FIG.1I 4T1
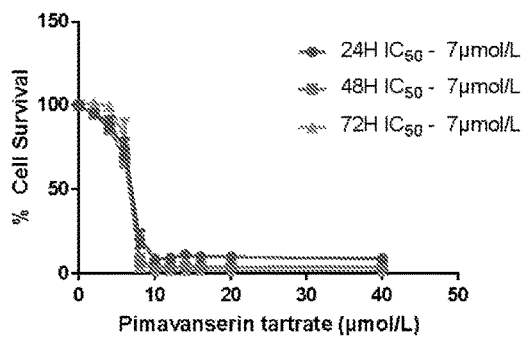
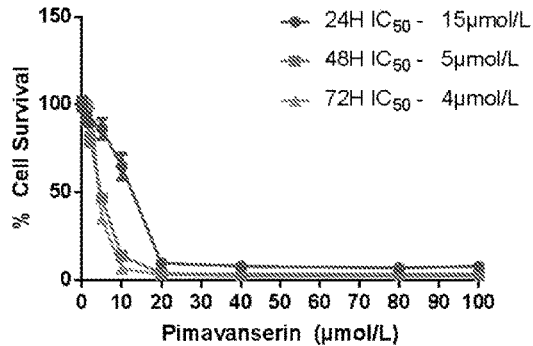

FIG.2A
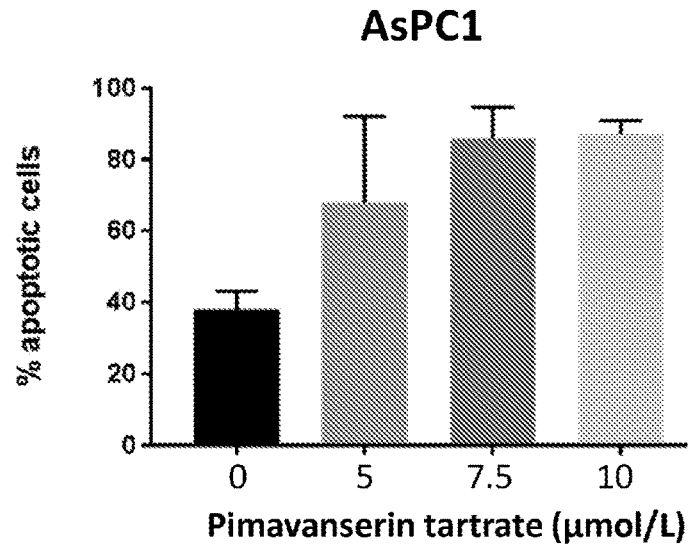
FIG.2B
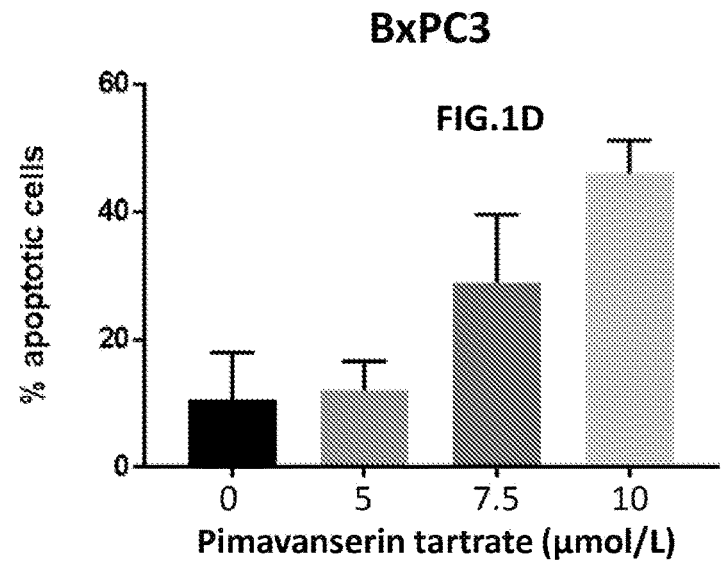
FIG.1D
FIG.2C
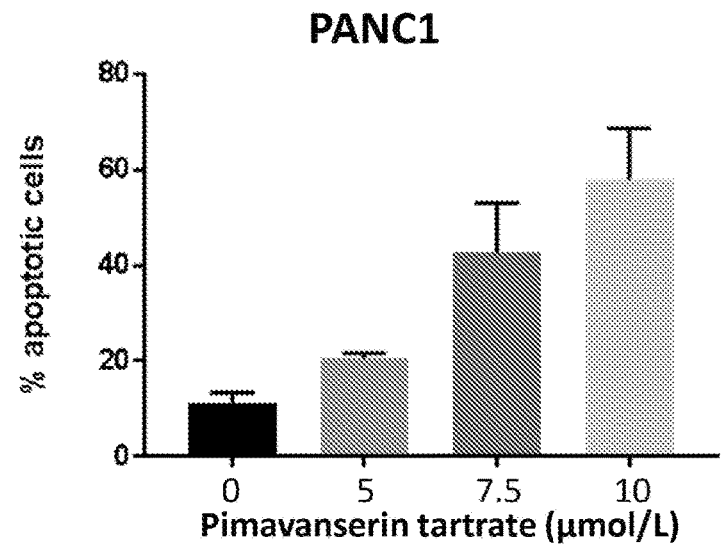

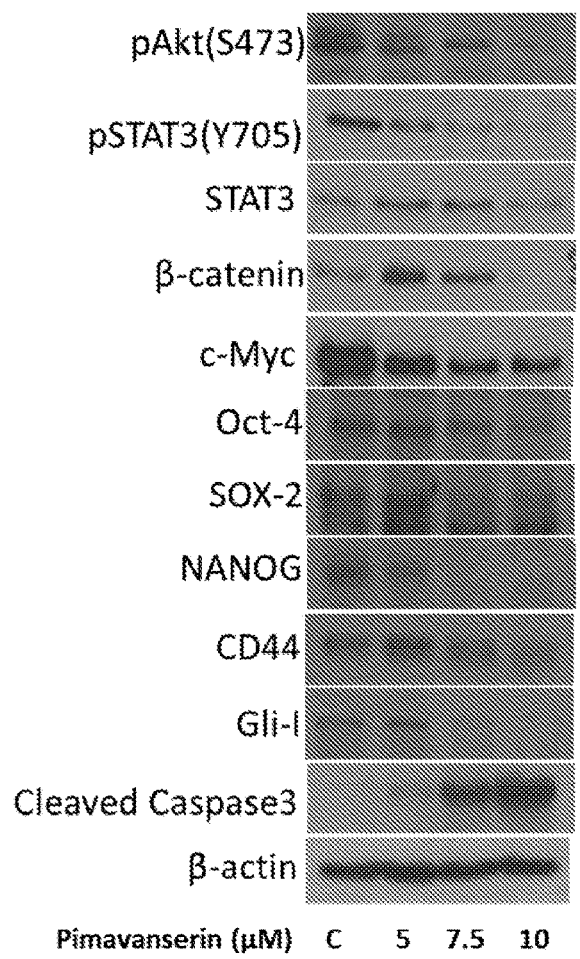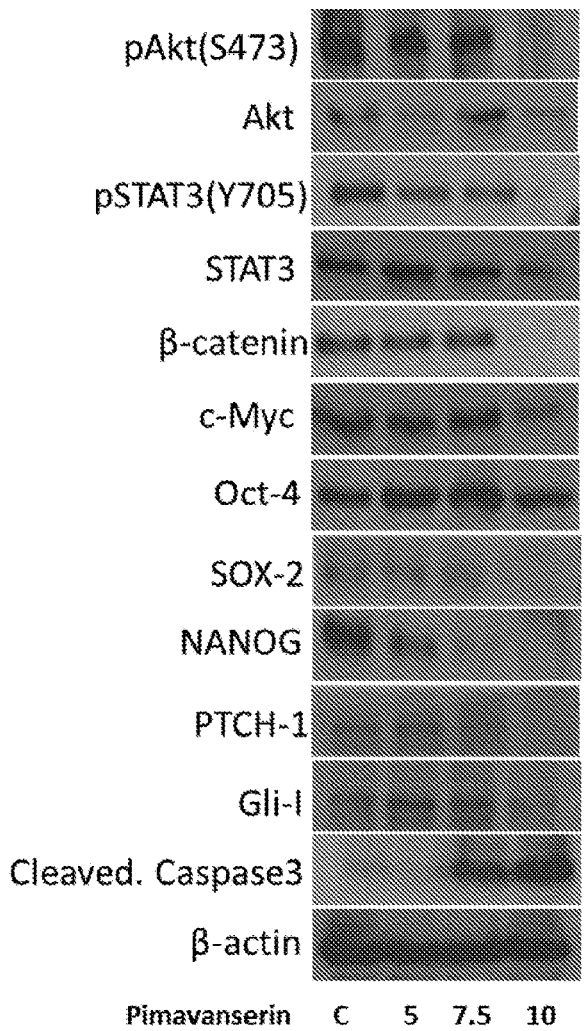

Control

Pimavanserin tartrate

COMPOSITIONS AND METHODS FOR TREATING CANCER

CROSS-REFERENCE TO RELATED APPLICATIONS

This application is the National Stage of International Application No. PCT/US2018/060763, filed on Nov. 13, 2018 claiming the priority of U.S. Provisional Application No. 62/585,080, filed on Nov. 13, 2017, the content of each of which is incorporated by reference herein.

TECHNICAL FIELD OF THE INVENTION

The present invention relates in general to the field of composition and methods for treating cancer, and more particularly, to a method of using and compositions that include Pimavanserin to treat cancers.

BACKGROUND OF THE INVENTION

Without limiting the scope of the invention, its background is described in connection with treating, e.g., pancreatic cancer. Cancer is known to cause a global burden of 21.7 million new cases and 13 million cancer deaths by 2030. In 2012, more than 50% of the diagnosed cancer cases died worldwide due to the constraints prevailing in the treatment. As such, it is becoming vital to develop new options for cancer treatment.

Pancreatic cancer typically occurs as pancreatic ductal adenocarcinoma and is one of the most aggressive and devastating disease. Despite of the modern era in cancer research, pancreatic cancer has proven to be one of the most fatal malignancies, making it the fourth leading cause of cancer related deaths in the United States (1). Owing to the poor prognosis of patients diagnosed with advanced pancreatic cancer, the median survival of pancreatic cancer patients is estimated to be about 6 months. The multifactorial nature and aberrant high frequencies of mutations makes it more fatal and resistant to current therapeutic options. The success of conventional chemotherapies is also dismal making the patients succumb to debilitating effects. Treatment strategies that target the factors involved in the obstacles of pancreatic cancer treatment might therefore have the potential to improve the therapeutic management of this lethal disease (1, 2).

One such method for treating, e.g., pancreatic cancer, is taught in U.S. Pat. No. 9,758,786, issued to Trieu, and entitled "Compositions and methods for treating pancreatic cancer." Briefly, this patent is said to teach compositions for sensitizing tumors to anti-tumor therapies. The compositions are said to include antisense oligonucleotides against TGF-β2, wherein the compositions sensitize tumors to anti-tumor therapies.

Another such treatment is taught in U.S. Pat. No. 9,717,724, issued to Bayever, et al., entitled, "Methods for treating pancreatic cancer using combination therapies." Briefly, these inventors are said to teach methods for treating pancreatic cancer in a patient by administering liposomal irinotecan (MM-398) alone or in combination with additional therapeutic agents, e.g., the liposomal irinotecan (MM-398) is co-administered with 5-fluorouracil and leucovorin.

Despite these developments, a need remains for effective treatments for cancer that, preferably, have few if any side effects. Therefore, a need remains for novel composition and methods for treating cancers, e.g., pancreatic, skin, colon and skin cancers.

SUMMARY OF THE INVENTION

In one embodiment, the present invention includes a method of treating a cancer comprising administering to a subject a pharmaceutical composition comprising Pimavanserin, active polymorphs, analogs, or salts thereof in an amount sufficient to treat the cancer in the subject and a pharmaceutically acceptable carrier. In one aspect, the cancer is a pancreatic, skin, colon, liver, breast, oesophageal, lung cancer, head and neck cancer, ovarian cancer, renal cell carcinoma, glioblastoma, neuroblastoma, medulloblastoma, astrocytoma, brain stem glioma and other brain tumors. In another aspect, the Pimavanserin, active polymorphs, analogs, or salts thereof kills cancer cells selected from pancreatic, skin, colon, liver, lung, oesophageal, breast cancer, head and neck cancer, ovarian cancer, renal cell carcinoma, glioblastoma, neuroblastoma, medulloblastoma, astrocytoma, brain stem glioma and other brain tumors. In another aspect, the subject is an animal. In another aspect, the step of administering results in at least one of the following: a 10% reduction in size of tumors, at least a 10% reduction in number of cancer metastases, at least a 10% increase in activity of immune system against the cancer cells, or at least a 10% improvement in clinical signs and symptoms related to cancer. In another aspect, the cancer is a lung cancer. In another aspect, the cancer is a skin cancer. In another aspect, the e cancer is a melanoma selected from an advanced melanoma, an unresectable melanoma, a metastatic melanoma, a melanoma with a BRAF mutation, a melanoma with an NRAS mutation, a cutaneous melanoma, or an intraocular melanoma. In another aspect, the cancer is a pancreatic cancer. In another aspect, the pancreatic cancer is an exocrine tumor. In another aspect, the exocrine tumor is selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors. In another aspect, the pancreatic cancer is a neuroendocrine tumor. In another aspect, the neuroendocrine tumor is selected from the group consisting of gastrinoma (Zollinger-Ellison Syndrome), glucagonoma, insulinoma, nonfunctional islet cell tumor, somatostatinoma, and vasoactive intestinal peptide-releasing tumor (VIPoma or Verner-Morrison Syndrome). In another aspect, the pancreatic cancer is adenocarcinoma. In another aspect, the pancreatic cancer is hypoxic. In another aspect, the pancreatic cancer is non-hypoxic. In another aspect, the cancer is a breast cancer. In another aspect, the breast cancer is a triple negative breast cancer. In another aspect, the cancer is a colorectal cancer. In another aspect, the cancer is a MSI-high (high microsatellite instability) cancer. In another aspect, the cancer is liver, lung, oesophageal cancer, ovarian cancer, renal cell carcinoma, head and neck cancer. In another aspect, the cancer is brain tumors including glioblastoma, neuroblastoma, medulloblastoma, astrocytoma, brain stem glioma and other brain tumors. In another aspect, the Pimavanserin, active polymorphs, analogs, or salts thereof has no side effects. In another aspect, the cancer is a metastatic cancer. In another aspect, the Pimavanserin, active polymorphs, analogs, or salts thereof is adapted for oral, enteral, parenteral, intravenous, pulmonary, nasal, or rectal administration. In another aspect, the Pimavanserin, active polymorphs, or analogs thereof is provided in the form of a salt selected from at least one of a phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, tartrate or naphthalenesulfonate. In another aspect, the Pimavanserin is N-(4-fluorophenylmethyl)-N-(1-methylpiperidin-4-yl)-N'-(4-(2-methylpropyloxy)phenylmethyl)carbamide. In another aspect, the method further comprises providing one or more chemotherapeutic agents or any other agent, wherein the Pimavanserin, active polymorphs, analogs, or salts thereof enhances that activity of the one or more chemotherapeutic agents. In another aspect, the method further comprises providing one or more immunotherapeutic agents, wherein the Pimavanserin, active polymorphs, analogs, or salts thereof enhances that activity of the one or more immunotherapeutic agents. In another aspect, the method further comprises determining if the cancer is under normoxic or hypoxic conditions. In another aspect, the method further comprises identifying one or more oncogenic signaling pathways in the cancer, and selecting one or more chemotherapeutic agents, one or more immunotherapeutic agents, or an agent, that block the more oncogenic signaling pathways in the cancer. In another aspect, the composition further comprises one or more chemotherapeutic, targeted therapeutic agents, wherein the Pimavanserin, active polymorphs, and analogs thereof enhances that activity of the one or more chemotherapeutic agents. In another aspect, the composition further comprises one or more immunotherapeutic agents, wherein the Pimavanserin, active polymorphs, and analogs thereof enhances that activity of the one or more immunotherapeutic agents. In another aspect, the composition further comprises one or more chemotherapeutic agents, one or more targeted therapeutic agents, one or more immunotherapeutic agents, or an agent, that are selected to block one or more oncogenic signaling pathways in the cancer. In another aspect, the composition further comprises one or more micro-RNAs, wherein the Pimavanserin, active polymorphs, and analogs thereof modulates miRNAs in the cancer. In another aspect, the composition is provided radiation, wherein Pimavanserin, active polymorphs, and analogs thereof radio-sensitize the cells to overcome radiation resistance. In another aspect, the cancer is an alcohol mediated cancer, wherein Pimavanserin, active polymorphs, and analogs thereof prevent or treat alcohol-mediated cancer.

In another embodiment, the present invention includes a composition for treating a cancer comprising administering to a subject a pharmaceutical composition comprising Pimavanserin, active polymorphs, analogs, or salts thereof provided in an amount sufficient to treat the cancer in the subject and a pharmaceutically acceptable carrier. In one aspect, the Pimavanserin, active polymorphs, analogs, or salts thereof are provided in an amount of greater than 5 mg/kg of body weight. In another aspect, the Pimavanserin, active polymorphs, analogs, or salts thereof is provided with one or more agents that prevent QT prolongation. In another aspect, the Pimavanserin, active polymorphs, analogs, or salts thereof are provided in an amount sufficient to treat is a pancreatic, skin, colon or breast cancer. In another aspect, the Pimavanserin, active polymorphs, analogs, or salts thereof kills cancer cells selected from pancreatic, skin, colon, liver, lung, oesophagus, kidney, head and neck, renal cell carcinoma, ovarian cancer, glioblastoma, neuroblastoma, medulloblastoma, astrocytoma, brain stem glioma and other brain tumors or breast cancer cells. In another aspect, the step of administering results in at least one of the following: a 10% reduction in size of tumors, at least a 10% reduction in number of cancer metastases, at least a 10% increase in activity of immune system against the cancer cells, or at least a 10% improvement in clinical signs and symptoms related to cancer. In another aspect, the cancer is a melanoma. In another aspect, the cancer is a melanoma selected from an advanced melanoma, an unresectable melanoma, a metastatic melanoma, a melanoma with a BRAF mutation, a melanoma with an NRAS mutation, a cutaneous melanoma, or an intraocular melanoma. In another aspect, the cancer is a pancreatic cancer. In another aspect, the pancreatic cancer is an exocrine tumor. In another aspect, the exocrine tumor is selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors. In another aspect, the pancreatic cancer is a neuroendocrine tumor. In another aspect, the neuroendocrine tumor is selected from the group consisting of gastrinoma (Zollinger-Ellison Syndrome), glucagonoma, insulinoma, nonfunctional islet cell tumor, somatostatinoma, and vasoactive intestinal peptide-releasing tumor (VIPoma or Verner-Morrison Syndrome). In another aspect, the pancreatic cancer is adenocarcinoma. In another aspect, the pancreatic cancer is hypoxic. In another aspect, the pancreatic cancer is non-hypoxic. In another aspect, the cancer is a breast cancer. In another aspect, the breast cancer is a triple negative breast cancer. In another aspect, the cancer is a colorectal cancer. In another aspect, the cancer is a MSI-high (high microsatellite instability) cancer. In another aspect, the treatment has no side effects. In another aspect, the cancer is a metastatic cancer. In another aspect, the Pimavanserin, active polymorphs, analogs, or salts thereof is adapted for oral, enteral, parenteral, intravenous, pulmonary, nasal, or rectal administration. In another aspect, the Pimavanserin, active polymorphs, or analogs thereof is provided in the form of a salt selected from at least one of phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, or tartrate, naphthalenesulfonate. In another aspect, the Pimavanserin is N-(4-fluorophenylmethyl)-N-(1-methylpiperidin-4-yl)-N'-(4-(2-methylpropyloxy)phenylmethyl)carbamide. In another aspect, the method further comprises identifying one or more oncogenic signaling pathways in the cancer, and selecting one or more chemotherapeutic agents, one or more immunotherapeutic agents, or an agent, that block the more oncogenic signaling pathways in the cancer. In another aspect, the composition further comprises one or more chemotherapeutic, targeted therapeutic agents, wherein the Pimavanserin, active polymorphs, and analogs thereof enhances that activity of the one or more chemotherapeutic agents. In another aspect, the composition further comprises one or more immunotherapeutic agents, wherein the Pimavanserin, active polymorphs, and analogs thereof enhances that activity of the one or more immunotherapeutic agents. In another aspect, the composition further comprises one or more chemotherapeutic agents, one or more targeted therapeutic agents, one or more immunotherapeutic agents, or an agent, that are selected to block one or more oncogenic signaling pathways in the cancer. In another aspect, the composition further comprises one or more micro-RNAs, wherein the Pimavanserin, active polymorphs, and analogs thereof modulates miRNAs in the cancer. In another aspect, the composition is provided radiation, wherein Pimavanserin, active polymorphs, and analogs thereof radio-sensitize the cells to overcome radiation resistance. In another aspect, the cancer is an alcohol mediated cancer, wherein Pimavanserin, active polymorphs, and analogs thereof prevent or treat alcohol-mediated cancer.

In another aspect, the composition further comprises one or more chemotherapeutic agents, wherein the Pimavanserin, active polymorphs, analogs, or salts thereof enhances that activity of the one or more chemotherapeutic agents. In another aspect, the composition further comprises one or more immunotherapeutic agents, wherein the Pimavanserin, active polymorphs, analogs, or salts thereof enhances that activity of the one or more immunotherapeutic agents. In another aspect, the composition further comprises one or more chemotherapeutic agents, one or more immunotherapeutic agents, or an agent, that are selected to block one or more oncogenic signaling pathways in the cancer.

In another embodiment, the present invention includes a method of treating a pancreatic, skin, colon liver, lung, oesophageal, head and neck cancer, ovarian cancer, renal cell carcinoma, glioblastoma, neuroblastoma, medulloblastoma, astrocytoma, brain stem glioma, and other brain tumors or breast cancer comprising administering to a subject a pharmaceutical composition comprising Pimavanserin, active polymorphs, analogs, or salts thereof in an amount sufficient to treat the reproductive cancer in the subject and a pharmaceutically acceptable carrier.

In yet another embodiment, the present invention includes a method of evaluating a Pimavanserin, active polymorphs, analogs, or salts thereof believed to be useful in treating a cancer, the method comprising: administering the Pimavanserin, active polymorphs, analogs, or salts thereof to a first subset of cancer cells, and a placebo to a second subset of cancer cells; and determining if the Pimavanserin, active polymorphs, analogs, or salts thereof reduces the number of cancer cells that is statistically significant as compared to any reduction occurring in the second subset of cancer cells, wherein a statistically significant reduction indicates that the Pimavanserin, active polymorphs, analogs, or salts thereof is useful in treating that cancer.

DESCRIPTION OF THE DRAWINGS

For a more complete understanding of the features and advantages of the present invention, reference is now made to the detailed description of the invention along with the accompanying figures and in which:

FIGS. 2A to 2C shows the effect of Pimavanserin tartrate in inducing apoptosis in pancreatic cancer cells in a concentration dependent manner. Briefly, the following cells were treated at $0.2\times10^6$, in FIG. 2A AsPC1 cells, FIG. 2B BxPC3 cells, and in FIG. 2C PANC1 cells, which were plated and treated with 5, 7.5 and 10 µM pimavanserin tartrate for 48 hours. Percent apoptotic cells was evaluated by AnnexinV/FITC apoptosis assay using Accuri C6 flow cytometer. Studies were repeated independently 3 times.

FIGS. 3A to 3D show that treatment with Pimavanserin tartrate inhibits sonic hedgehog signaling and Akt/STAT3/GLI1 signaling. Briefly, in FIG. 3A AsPC1 cells, FIG. 3B BxPC3 cells, FIG. 3C PANC1 cells, and FIG. 3D MIAPaCa2 cells, were treated with 5, 7.5 and 10 µM pimavanserin tartrate for 48 hours. Representative blots showing a concentration-dependent effect of pimavamserin tartrate on pAkt(S473), pSTAT3(Y705), c-Myc, Oct-4, SOX-2, NANOG, CD44, GLI1, cleaved caspase3. β-actin was used as a loading control. Figures shown are the representative blots of at least three independent tests.

FIG. 4B orthotopic tumors were aseptically removed and the tumor size was compared between control and pimavanserin treated group. In FIG. 4C mice weight was recorded once in 10 days. The average weight of the mice is plotted against days. Values are plotted as mean±SEM.

In FIG. 5A tumor luminescence was measured about twice a week and plotted against days. Values are plotted as mean±SEM. In FIG. 5B orthotopic tumors were aseptically removed and the tumor size was compared between control and pimavanserin tartrate treated group. FIG. 5C shows representative mouse from control and pimavanserin tartrate treated group. FIG. 5D shows individual tumors were weighed and the results were plotted as mean±SEM. FIG. 5E shows mice weight was recorded once in a week. The average weight of the mice is plotted against days. Values are plotted as mean±SEM. FIG. 5F shows representative blots showing the effect of pimavamserin tartrate on the listed proteins.

FIG. 6B horizontal activity' FIG. 6C vertical activity; and FIG. 6D ambulatory activity. Values are plotted as mean±SEM.

DESCRIPTION OF THE INVENTION

Figure 1J:
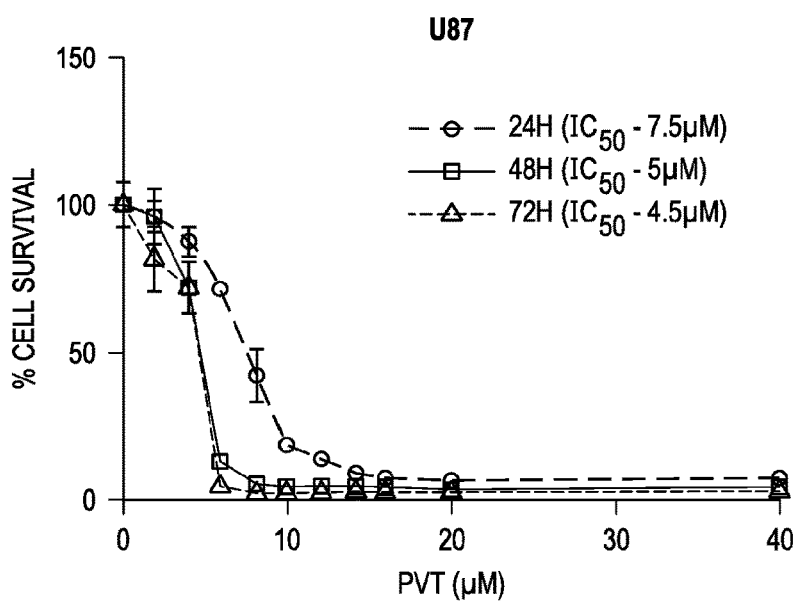
FIGS. 1A to 1E show the effect of Pimavanserin tartrate suppresses the cell survival of pancreatic cancer cells.
FIGS. 1F to 1G show the effect of pimavanserin tartrate suppresses the cell survival of melanoma cells.
FIG. 1H and FIG. 1I shows the anti-proliferative effects of pimavanserin tartrate in colon cancer and breast cancer cells respectively. In the figures, the following cancer cells were evaluated: AsPC1 cells (FIG. 1A), BxPC3 cells (FIG. 1B), PANC1 cells (FIG. 1C), MIAPaCa2 cells (FIG. 1D), PO2 cells (FIG. 1E), A375VR cells (FIG. 1F), SKMEL-28 cells (FIG. 1G), HCT-116 cells (FIG. 1H), 4T1 cells (FIG. 1I), U87 cells (FIG. 1J), U251 cells (FIG. 1K), T98G vells (FIG. 1L), CT2A cells (FIG. 1M) which were treated with varied concentrations of pimavanserin tartrate for 24, 48 and 72 hours. Cell survival was determined by sulforhodamine B assay to estimate the $IC_{50}$ values. The studies were repeated independently for three times with 4 replicates in each test. Values are plotted as mean±SD and the statistical significance level was considered as $p<0.05$.
Figure 1K:
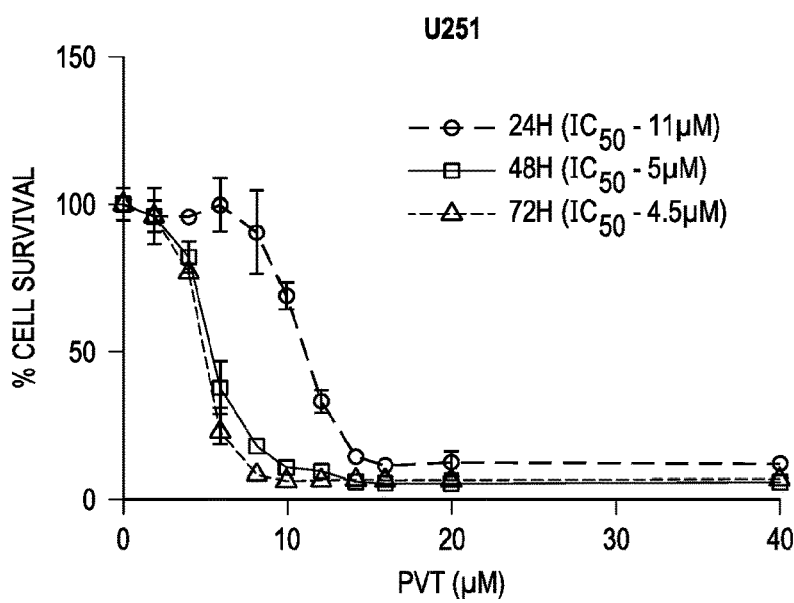
Figure 1L:
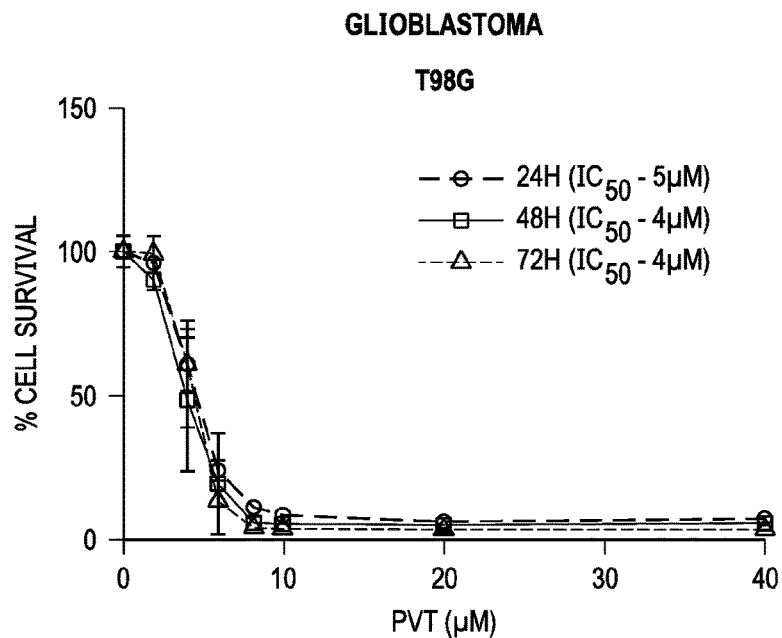
Figure 1M:
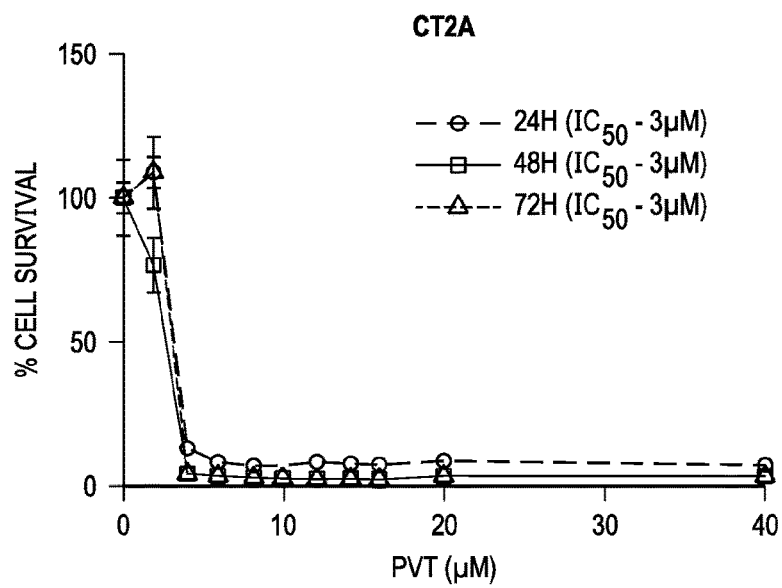

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, Pimavanserin is N-(4-fluorophenylmethyl)-N-(1-methylpiperidin-4-yl)-N'-(4-(2-methylpropyloxy)phenylmethyl)carbamide, also known as N-(1-methylpiperidin-4-yl)-N-(4-flourophenylmethyl)-N'-(4-(2-methylpropyloxy)phenylmethyl)carbamide, or active polymorphs thereof, such as those taught in U.S. Pat. No. 7,713,995, relevant portions incorporated herein by reference. The Pimavanserin or active polymorphs thereof may be provided in a form salt selected from at least one of a phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, tartrate or naphthalenesulfonate.

Surprisingly, it was found that Pimavanserin has a significant growth suppressive effect against several cancers, including: melanoma, pancreatic, colon, glioblastoma and breast cancer cells and the results were promising. The present invention includes methods and composition that include Pimavanserin and its derivatives for the treatment and killing of human melanoma, pancreatic, colon, glioblastoma and breast cancer cells. Pimavanserin and its derivatives are soluble in all solvents including water and owing to its enhanced solubility, it nullifies the solubility issues. Furthermore, many anti-cancer compounds fail to cross the blood brain barrier and exert serious side effects. Pimavanserin and its derivatives have an enhanced safety and tolerability profile, which avert the issues of side effects and provides effective cancer treatment with reduced side effects. In addition, Pimavanserin and its derivatives can cross the blood brain barrier and prevent brain metastasis and brain cancer, which will pave way for a new generation of cancer treatments.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the cancer therapy. The present invention is demonstrated herein to have an effect against, at least, pancreatic cancer, colon cancer, liver, oesophageal, lung, head and neck, ovarian, renal cell carcinoma, glioblastoma, neuroblastoma, medulloblastoma, astrocytoma, colorectal, brain stem glioma and other brain tumors, breast cancer, and skin cancer.

As used herein, the term "therapeutically effective amount" refers to an amount of a compound of the invention that is effective when administered alone or in combination to treat the desired condition or disorder. A "therapeutically effective amount" includes an amount of the combination of compounds claimed that is effective to treat the desired condition or disorder. The combination of compounds can be additive and is preferably a synergistic combination. Synergy occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

As used herein, the term "pharmaceutically acceptable salts" refers to derivatives of the disclosed compounds, wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palimitic, pamoic, pantothenic, phenylacetic, phosphoric, polygalacturonic, propionic, salicyclic, stearic, succinic, sulfamic, sulfanilic, sulfuric, tannic, tartaric, toluenesulfonic, and valeric.

The present inventors have found that that among several oncogenic signaling pathways, Hedgehog signaling plays a pivotal role in conferring malignant phenotype and significantly drives pancreatic cancer progression (3). It has been reported that, targeting hedgehog signaling will improve the treatment outcomes of patients with refractory pancreatic cancer. Sonic hedgehog (SHH) signaling is a hallmark of pancreatic cancer and it was discovered to be overexpressed in 70% of PDAC tissues (3). Oncogenic mutation of KRAS gene (found in >90% of pancreatic cancer cases) leads to the secretion of hedgehog ligand proteins and activates the downstream effector GLI1 (a transcriptional factor in sonic hedgehog signaling) (4). Overexpression of GLI1 has been significantly attributed to poor prognosis and patient survival in resected PDAC (5). In addition, aberrant expression of GLI1 results in invasion, metastasis, chemo-resistance and epithelial-mesenchymal transition in various cancer models including pancreatic cancer (6, 7). Moreover, SHH signaling is responsible for imparting stem cell properties to pancreatic cancer cells (2).

Further, the present inventors recognized that schizophrenic patients taking antipsychotic medications have been reported to show reduced incidence of cancer. Anti-psychotic drugs such as risperidone, pimozide, haloperidol, olanzapine, chlorpromazine and reserpine have been demonstrated to act on cholesterol homeostasis and exert anti-neoplastic effects in various cancer models (8). The present inventors have reported the anti-cancer effects of penfluridol (an anti-psychotic drug prescribed for the treatment of schizophrenia) in various cancer models including pancreatic cancer (7, 9, 10, 11, 12). Moreover, trifluoperazine has been shown to improve pancreatic cancer therapy (13).

Pimavanserin is a highly selective inverse agonist of 5-HT2A serotonin receptors. It is an oral anti-psychotic drug approved by the FDA in May 2016 for the treatment of Parkinson's disease psychosis (PDP). In the current study, the present inventors found significant growth suppression and apoptosis with pimavanserin treatment in pancreatic cancer cells. These results indicate that pimavanserin treatment modulated sonic hedgehog signaling markers in various pancreatic cancer cells. Oral administration of pimavanserin significantly suppressed the tumor growth of xenograft and orthotopic pancreatic tumors. Moreover, Pimavanserin did not show any general signs of toxicity and no apparent changes were observed in the behavioral activity of mice. These studies are the first to demonstrate the anti-cancer effects of pimavanserin.

Cell culture. Human pancreatic cancer cell lines AsPC1, BxPC3, PANC1, MIAPaCa2 cells, SKMEL-28 human melanoma cells, U87, U251, T98G human glioblastoma cells, and human colon cancer cell line HCT-116 were purchased from ATCC (Rockville, Md.). CT2A murine glioblastoma cells was a kind gift from Dr. Jill Edgar, Boston College, Boston. Cell lines were authenticated by STR analysis at TTUHSC core facilities (Lubbock, Tex.). Monolayer cultures of AsPC1 and BxPC3 cells were maintained in RPMI medium whereas PANC1, PANC1-luc, U251, T98G, CT2A cells were cultured in DMEM medium and U87 cells were cultured in MEM medium, supplemented with 10% fetal bovine serum, 1% penicillin-streptomycin antibiotic mixture, 2 mM L-glutamine, 10 mM HEPES, 1 mM sodium pyruvate, 2.2 g/L sodium bicarbonate and 10 ml/L glucose. All the cells were cultured at 370 C incubator of 95% air and 5% CO2.

Cytotoxicity studies. The cytotoxic effects of pimavanserin tartrate in AsPC1, BxPC3, PANC1, MIAPaCa2, PO2, A375VR, SKMEL-28, HCT-116, 4T1, U87, U251, T98G, CT2A cells were determined by sulforhodamine B (SRB) assay. Cells were plated at a density of 3,000-4,000 cells per well in 96 well plates and allowed to attach overnight. Post overnight incubation, the cells were treated with different concentrations of pimavanserin (Selleck Chemicals) for 24, 48 and 72 hours. After desired duration of treatment (24, 48 and 72 hours), cells were fixed by 10% ice-cold trichloroacetic acid. Consequently, plates were washed gently with water and the live cells were stained by SRB dye for 2 hours followed by washing with 1% solution of acetic acid. The plates were allowed to dry for 30 minutes and the SRB stained cells were dissolved in 10 mmol/L Tris-base solution. The optical density was measured using plate reader (Biotek instruments) as described by the present inventors (12).

AnnexinV/FITC apoptosis assay. The effects of pimavanserin in inducing apoptosis were assessed by AnnexinV/FITC apoptosis assay. The assay was performed by FITC AnnexinV apoptosis detection kit (BD biosciences, San Jose, Calif., USA). Briefly, $0.2 \times 10^6$ pancreatic cancer cells were plated in each well of 6-well plate and incubate overnight for the cells to attach. The cells were then treated with varying concentrations of pimavanserin tartrate. After 48 hours, cells were trypsinized and suspended in PBS. Cells were washed and re-suspended in 150 µl of annexin binding buffer. The cells were then stained with 4 µl AnnexinV FITC and 4 µl propidium iodide for 20 minutes in dark. Post incubation, the volume was adjusted to 350 µl by adding annexin binding buffer. Samples were then analyzed by flow cytometer (Accuri C6, AnnArbor, Mich., USA) as previously described by the present inventors (7).

Western blot analysis. AsPC1, BxPC3, PANC1, and MIAPaCa2 cells were treated with varying concentrations of pimavanserin tartrate for 48 hours. After 48 hours, cells were collected and subjected to PBS wash twice. The whole cell lysates were prepared using 4% (w/v) CHAPS in urea-tris buffer. Protein content in the lysates were estimated using Bradford reagent (Bio-rad, California, USA). 40 µg of protein from whole cell lysates were subjected to SDS-PAGE and the resolved proteins were transferred onto PVDF membrane. The membranes were probed for primary antibodies against pSTAT3(Y705), pAkt(S473), β-catenin, c-Myc, OCT4, SOX-2, NANOG, CD44, GLI1, cleaved caspase-3 and β-actin. All primary antibodies were procured from Cell Signaling Technologies (Danvers, Mass.) except β-actin (Sigma Aldrich, St. Louis, Mo.). Dilution factor was 1:1000 for all the antibodies from Cell Signaling and 1:2000 for β-actin antibody. The membranes were developed as described by the present inventors (16).

Pancreatic tumor xenograft model. Female athymic nude mice (4-6 week old) were purchased from Harlan Laboratory (Livermore, Calif.). All the experiments were performed under the strict compliance and regulations approved from Institutional Animal Care and Use Committee (IACUC), Texas Tech University Health Sciences Center, Amarillo, Tex. $1 \times 10^6$ BxPC3 cells were implanted in right flank of the mice. Once tumor volume was observed to be 70 mm³, mice were randomly divided into two groups with 5 mice in each group. Group I was assigned as control group, which received the vehicle only (PBS). Group II mice received 10 mg/kg Pimavanserin tartrate by oral gavage everyday. Treatment with Pimavanserin was started at day 13. Tumor growth was monitored by measuring the tumor volume twice a week until day 40 using a Vernier caliper as described by the present inventors (11). The study was terminated at day 40 due to tumor burden. The mice were euthanized and the tumors were aseptically removed. A part of tumor was snap frozen for western blotting and the other part was fixed in formalin for immunohistochemistry and TUNEL analysis. Mice weight was monitored once in ten days.

Orthotopic pancreatic tumor model. 4-6 week old female athymic nude mice were used for orthotopic injection. All the experiments were performed under the strict compliance and regulations approved from Institutional Animal Care and Use Committee (IACUC), Texas Tech University Health Sciences Center, Amarillo, Tex. Mice were anesthetized by using isoflorane and a minor incision was made in the left abdomen. Stably transfected luciferase-expressing PANC1 (PANC1-luc) cells were orthotopically-implanted in the pancreas. $1 \times 10^6$ exponentially growing PANC1-luc cells in 20 µl PBS suspension were injected into the sub-capsular region on the pancreas using a 30-gauge sterile needle. The peritoneum and skin incisions were closed sequentially with absorbable suture. Buprenorphine was administered as a pain killer to mice at every 8 hours for 2 days. The growth of orthotopically-implanted tumors was monitored by measuring the luminescence by IVIS imaging (Calliper Life Sciences). In order to determine the basal luminescence value, mice were imaged on the same day after injecting luciferin (3 mg/mouse, i.p.). Mice were randomly divided into two groups (control and treatment) on day 17 after orthotopic injection of PANC1 luc cells. Control group received vehicle only whereas treatment group received 10 mg/kg pimavanserin tartrate by oral gavage everyday. The study was terminated at day 69 by humanely euthanizing the mice using $CO_2$ overdose. The mice was dissected and representative mouse from control and treatment groups were imaged for luminescence. The pancreas from control and treatment groups were aseptically excised out and snap frozen for western blot analysis, whereas few pancreas were fixed in formalin for immunohistochemical and TUNEL analysis. Mice weight was monitored once a week.

Mice behavioral analysis. In orthotopic studies, the behavioral activity of mice was analyzed after chronic administration of pimavanserin tartrate for 54 days. The behavioral analysis was performed by Versamax (Accuscan Instruments Inc., Columbus, Ohio, USA) as previously described by the present inventors (7, 12).

Statistical analysis. Statistical analysis was performed by Prism 7.0 software (GraphPad software Inc., San Diego, Calif.). Results are represented as means±standard deviation (SD) or standard error mean (SEM). Statistical significance was analyzed using Student's t-test and the outcomes were considered statistically significant at $p<0.05$.

All the animal studies were carried out in accordance with the ethical standards and according to approved protocol by Institutional Animal Care and Use Committee (IACUC).

Pimavanserin inhibited the proliferation of cancer cells, which included pancreatic cancer, melanoma, colon cancer, glioblastoma and breast cancer cells. The cytotoxic effects of pimavanserin were evaluated by SRB assay in the above mentioned cancer cells. The cells were treated with increasing concentrations of pimavanserin at 24, 48 and 72 hours. These results indicated that, treatment with pimavanserin resulted in significantly reduced survival of all cancer cell lines in a concentration and time dependent manner. The $IC_{50}$ of pimavanserin ranged from 7 to 15 µmol/L, 3 to 8 µmol/L and 3 to 8 µmol/L at 24, 48 and 72 hours respectively in all the cell lines (FIGS. 1A to 1M). These results suggest the potential cytotoxic effects of pimavanserin in pancreatic pancreatic cancer, melanoma, colon cancer, glioblastoma and breast cancer cells.

Figure 3C:
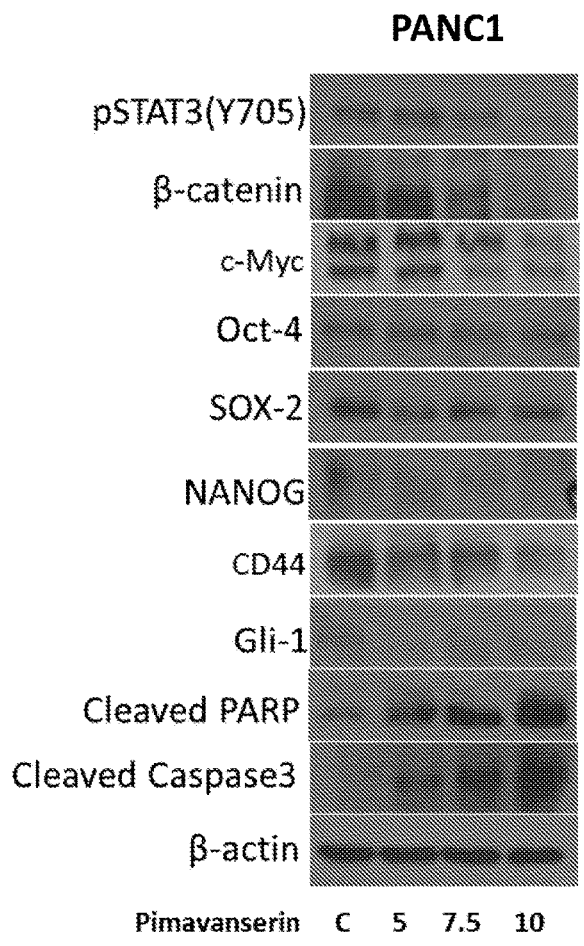

Pimavanserin induces apoptosis in pancreatic cancer cells. In order to determine the mechanism of anti-proliferative effects of pimavanserin tartrate, apoptosis induction by pimavanserin tartrate treatment was determined in AsPC1, BxPC3 and PANC1 pancreatic cancer cells by AnnexinV/FITC assay using flow cytometer. As shown in FIGS. 2A-2C, treatment of AsPC1, BxPC3 and PANC1 cells with varying concentrations pimavanserin for 48 hours resulted in significantly increased apoptosis. Treatment of AsPC1 and BxPC3 cells with 7.5 µM pimavanserin caused 2-fold increase in apoptotic cells (FIG. 2A, 2B), whereas in PANC1 cells, a 4-fold increase in apoptotic cells was observed (FIG. 2C). In addition, 10 µM pimavanserin treatment caused 5-fold increase in apoptotic cells in BxPC3 and PANC1 cells (FIG. 2B, 2C). Induction of apoptosis by pimavanserin treatment in AsPC1, BxPC3 and PANC1 cells was confirmed by cleavage of caspase 3 (FIGS. 3A-3C).

Figure 3D:
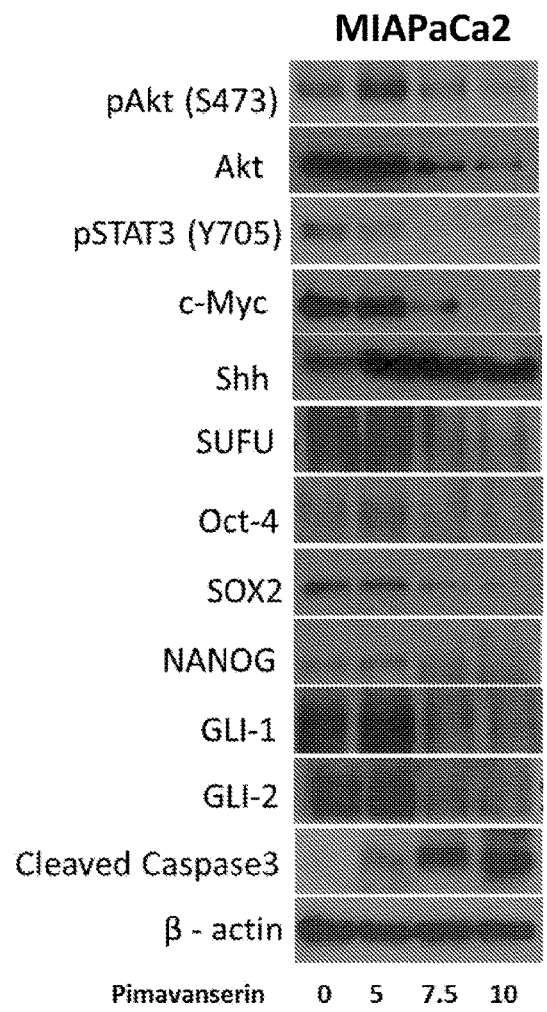

Inhibition of Akt, STAT3 and sonic hedgehog signaling by pimavanserin. Since significant growth suppressive effects and apoptosis by pimavanserin treatment were observed, the inventors further elucidated the molecular mechanism by which pimavanserin mediates the above-mentioned effects. The inventors performed western blot analysis using whole cell lysates from AsPC1, BxPC3, PANC1, and MIAPaCa2 cells treated with 0, 5, 7.5 and 10 µM pimavanserin for 48 hours. These results showed that pimavanserin treatment significantly inhibited the phosphorylation of STAT3 at Tyr705 and the expression of GLI1 in a concentration dependent manner in all the cell lines tested (FIGS. 3A-3D). In addition, the phosphorylation of Akt at Ser473 was significantly reduced in AsPC1, BxPC3, and MIAPaCa2 cells with pimavanserin treatment (FIGS. 3A, 3B, and 3D). Pimavanserin also reduced the expression of β-catenin in all the cell lines tested (FIGS. 3A-3C). Akt and STAT3 signaling modulates OCT-4, SOX-2, NANOG to activate GLI1, a transcription factor involved in sonic hedgehog signaling (7). Interestingly, the inventors also observed a remarkable inhibition in cancer stem cell markers OCT4, SOX-2, NANOG and CD44 (FIGS. 3A-3D). A significant cleavage of caspase 3 was observed in a concentration dependent manner in pancreatic cancer cells after 48 hours of pimavanserin treatment. These results indicate that pimavanserin suppresses cell survival and induces apoptosis by inhibiting Akt, STAT3 and sonic hedgehog signaling.

Figure 4A:
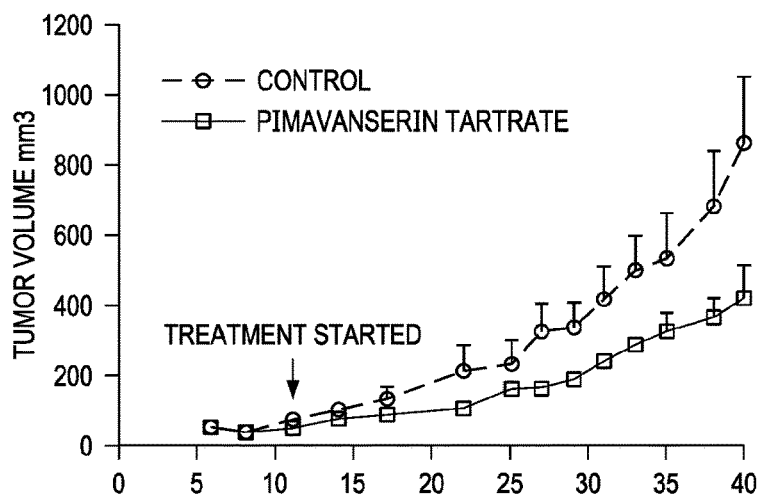
FIGS. 4A to 4C show that treatment with Pimavanserin suppresses the growth of pancreatic tumors in BxPC3 xenograft model and did not show any general signs of toxicity. Briefly, In FIG. 4A $1\times10^6$ BxPC3 cells in 1:1 mixture of PBS and matrigel were subcutaneously implanted in the right flank of 4-6 week old female athymic nude mice (n=5). 10 mg/kg pimavanserin tartrate was administered by oral gavage everyday, once the tumor volume was observed to be 70 $mm^3$. The treatment was given till day 40. Values are plotted as mean±SEM.
Figure 4B:
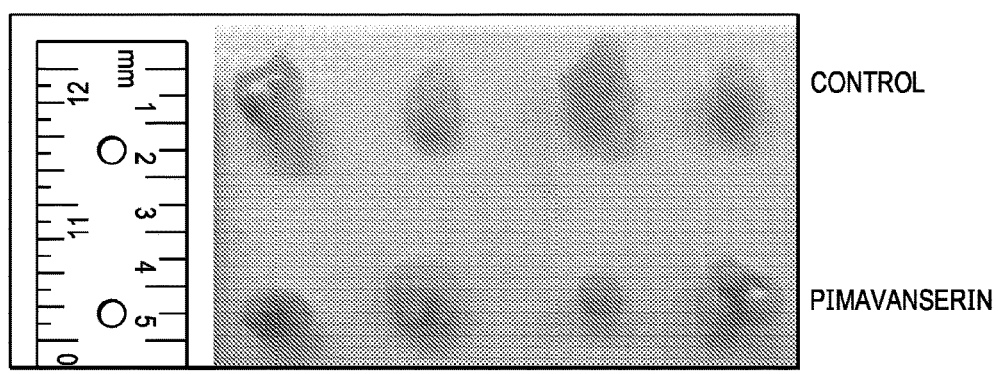
Figure 4C:
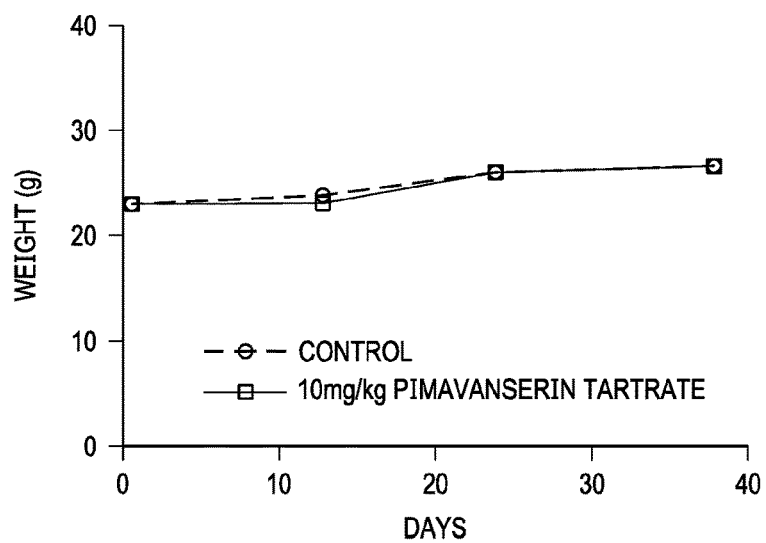

Pimavanserin suppresses the growth of subcutaneously implanted pancreatic tumors. To examine the in-vivo efficacy of pimavanserin and to establish the mechanism of tumor growth inhibition in pancreatic cancer, BxPC3 cells were implanted subcutaneously in female athymic nude mice. Once the tumor volume reached 70 mm³ in size, experimental group of mice were treated with 10 mg/kg pimavanserin by oral gavage everyday. These observations showed that, at the day of sacrifice the average tumor volume of control group was 873.395 mm3 whereas in the treatment group it was observed to be 429.01 mm3, indicating pimavanserin suppressed the growth of BxPC3 tumors by 50% (FIG. 4A). FIG. 4B orthotopic tumors were aseptically removed and the tumor size was compared between control and pimavanserin treated group. Furthermore, the overall weight of mice from control and treatment groups was similar throughout the study, which indicates that pimavanserin did not show any general signs of toxicity (FIG. 4C). These results indicate that pimavanserin displayed in-vivo efficacy in suppressing the pancreatic tumor growth.

Figure 5A:
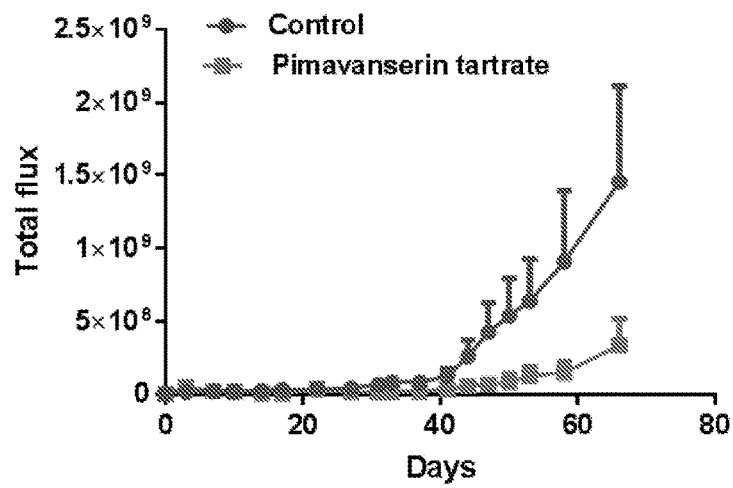
FIGS. 5A to 5F show that treatment with Pimavanserin tartrate suppresses the growth of orthotopically implanted pancreatic tumors in pancreas. $1\times10^6$ PANC-1 luc cells were surgically implanted on the pancreas of 4-6 week old female athymic nude mice (n=5). Mice were treated with 10 mg/kg pimavanserin tartrate at day 17 till day 69.
Figure 5B:
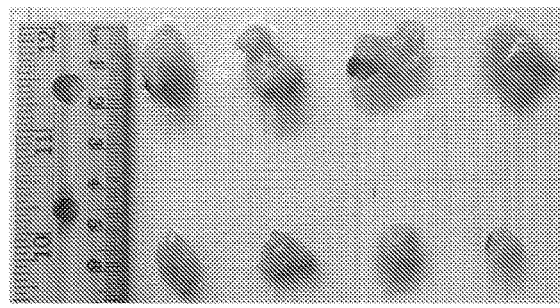
Figure 5C:
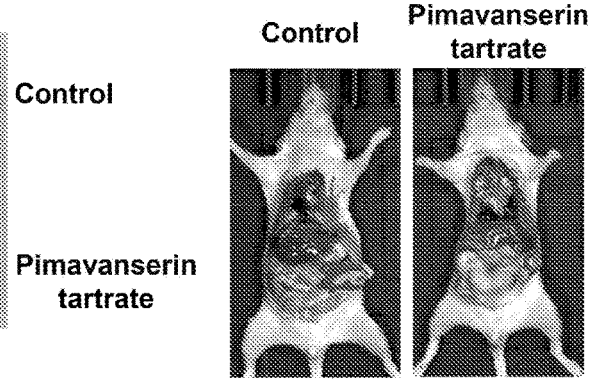
Figure 5D:
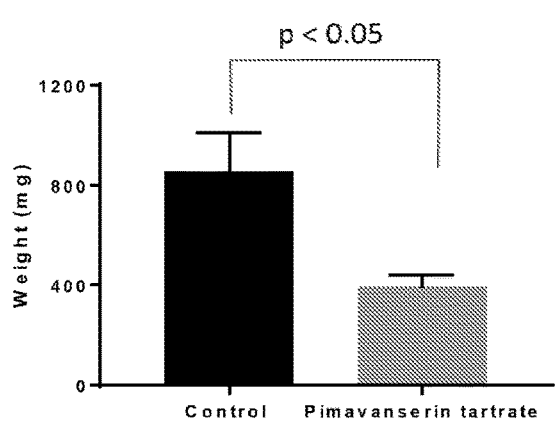
Figure 5E:
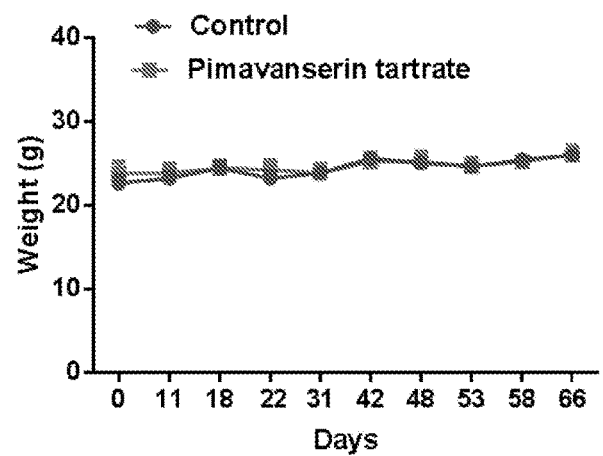
Figure 5F:
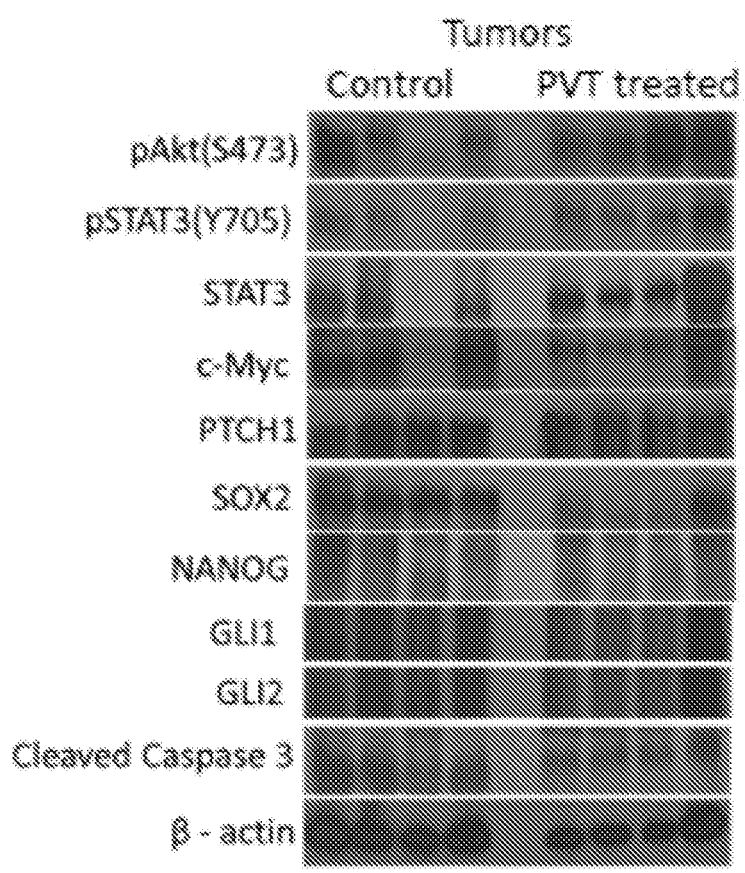
Figure 6A:
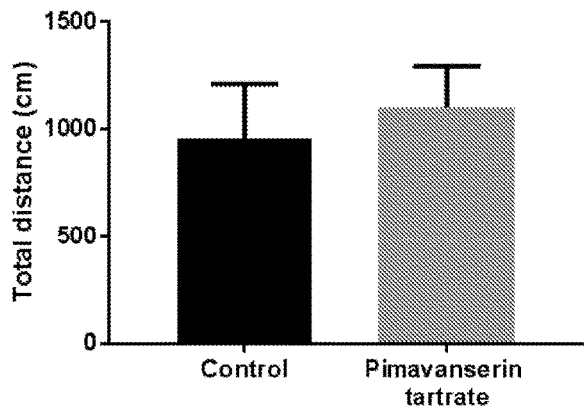
FIGS. 6A to 6D show that treatment with chronic administration of pimavanserin tartrate does not affect the behavioral activity of mice bearing orthotopically implanted pancreatic tumors. In orthotopic experiment, behavioral activity was measured using Versamax (Accuscan instruments) after 67 days of oral administration of 10 mg/kg pimavanserin tartrate. The following were measured, in FIG. 6A total distance.
Figure 6B:
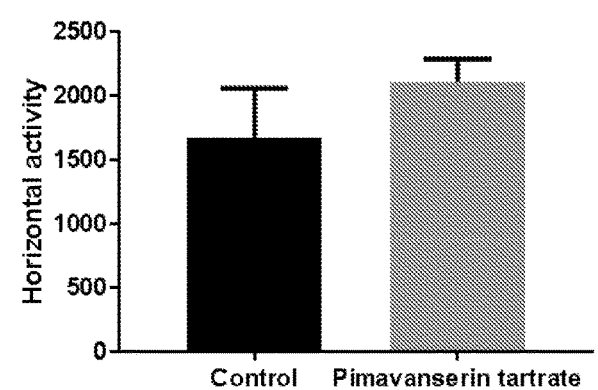
Figure 6C:
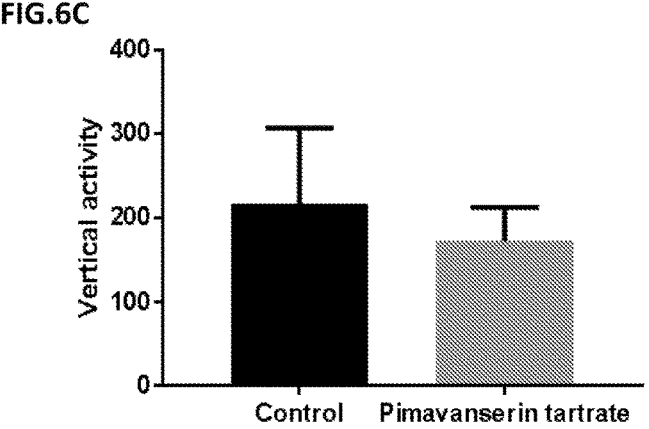
Figure 6D:
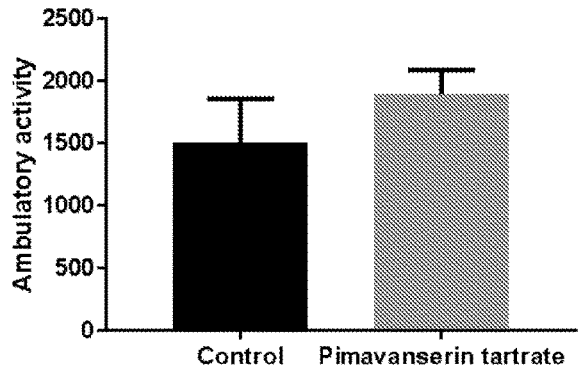

Pimavanserin inhibits the growth of orthotopic pancreatic tumors. In order to further validate the in-vivo efficacy of pimavanserin, PANC-1 luc cells were orthotopically implanted into the pancreas of athymic nude mice. After 17 days of tumor implantation, mice were treated with 10 mg/kg pimavanserin by oral gavage everyday. These results showed a constant increase in luminescence in the pancreas of control mice, whereas there was no steady and significant increase of luminescence in the pancreas of pimavanserin treated mice. However, at the end of the experiment the total flux in control group was observed as $1.45542 \times 10^9$ photons/second, while in treated group it was observed as $3.386 \times 10^8$ photons/sec, indicating 75% decrease of luminescence in the treated group when compared to the control group (FIG. 5A). These results suggest that pimavanserin tartrate suppressed 75% of orthotopic pancreatic tumor growth. After terminating the experiment, tumors were removed and weighed. The average weight of pimavanserin treated tumors was 46% less when compared to the tumors excised form control group (FIGS. 5B & 5D). Furthermore, the inventors also compared the luminescence between both the groups in isolated pancreas. These results clearly show that pimavanserin suppressed the tumor growth in the pancreas (see also FIG. 5A-FIG. 5D). In addition, pimavanserin did not reduce the overall weight of the mice when compared to the control group, which demonstrates the absence of general signs of toxicity by pimavanserin (FIG. 5E). FIG. 5F shows representative blots showing the effect of pimavanserin tartrate on the listed proteins.

Pimavanserin did not affect the behavioral activity of mice. Pimavanserin tartrate is an anti-psychotic drug used for the treatment of Parkinson disease. Owing to its action on the central nervous system, the behavioral activity of mice after long-term pimavanserin tartrate administration was assessed. The behavioral activity of mice was monitored after 67 days of 10 mg/kg pimavanserin treatment using Versamax (Accuscan Instruments Inc.). These results demonstrated that, pimavanserin tartrate did not change the behavioral activity parameters like total distance, horizontal activity, vertical activity and ambulatory activity when compared to control group mice (FIGS. 6A to 6D). These results show that chronic administration of pimavanserin did not affect the behavioral activity of mice and thus it is relatively safe for long-term use.

These results are the first report to elicit the anti-cancer effects of pimavanserin, an anti-psychotic drug used for the treatment of Parkinson's disease psychosis (PDP). The present disclosure shows both in-vitro and in-vivo evidence of the anti-neoplastic effects in pancreatic cancer, which is currently recognized as a fatal malignancy. Pimavanserin displayed remarkable anti-proliferative effects and apoptotic effects in pancreatic cancer cells. These effects were mediated by inhibition of Akt/STAT3/GLI1 signaling, and pimavanserin significantly inhibited the expression of key molecular players like pAkt(S473), pSTAT3(Y705), β-catenin, c-Myc, Oct-4, SOX-2, NANOG, CD44 and GLI1. In addition, pimavanserin increased the cleavage of caspase 3 as an indicator of apoptosis which further validates the observations made in FIGS. 2A, 2B and 2C. In order to evaluate the efficacy of pimavanserin in-vivo, the inventors used two different in-vivo models. Notably, pimavanserin suppressed the tumor growth in mice as evaluated by xenograft model and orthotopic model. Interestingly, pimavanserin was able to suppress 75% tumor growth in orthotopic model of pancreatic cancer, which demonstrates a novel treatment option for pancreatic cancer using a composition that has few, if any, side effects. Pimavanserin tartrate was able to suppress 50% tumor growth in a xenograft model. The oncogenic role of sonic hedgehog signaling and the role of GLI1 in pancreatic cancer has been studied. GLI1 overexpression has been significantly attributed to the complexity in pancreatic cancer (4, 5). Without wishing to be bound by theory, the data herein demonstrate that Pimavanserin tartrate exerts its anti-cancer effects by inhibiting the sonic hedgehog signaling and most importantly GLI1. In the course of these in-vivo studies, the anti-cancer dose of pimavanserin tartrate did not show any general signs of toxicity and side effects. The mice weight did not change in pimavanserin treatment group and was similar to the control group in both the in-vivo experiments. Most importantly, Pimavanserin treatment did not cause any apparent change in the behavioral activity of the mice as assessed by Versamax (Accuscan instruments). As such, pimavanserin is shown to be an anticancer drug for the treatment of pancreatic cancer. The heterogeneous property of pancreatic cancer and its aggressiveness warrants a need for a novel treatment option.

As used herein, the therapeutically effective amount of Pimavanserin or a pharmaceutically acceptable salt thereof are from about 0.1 to 5 mg per day, 1.0 to 10 mg per day, 1.0 to 25 mg per day, 10 to 25 mg per day, 10 to 50 mg per day, 50 to 500 mg per day, 100 to 450 mg per day, 200 to 400 mg per day, 300 to 500 mg per day, 350 to 500 mg per day, or 400 to 500 mg per day.

Cancer treatment methods must meet rigorous constraints before being approved by the FDA for administration to patients. Consequently, it is estimated that in 2012, more than 50% of the diagnosed cancer cases died worldwide due to these constraints preventing usage and treatment. It is becoming increasingly important to present more options for cancer treatment, and improve on existing methods to increase the likelihood of FDA acceptance.

Pimavanserin has been recently approved by the FDA to treat the hallucinations and delusions due to Parkinson's disease psychosis. The present invention demonstrates for the first time the anticancer effects of Pimavanserin against pancreatic, colon, glioblastoma, melanoma, breast cancer cell lines. It shows that Pimavanserin suppresses cancer cell survival in a concentration-dependent manner. Pimavanserin induces death in cancer cells by inhibiting key oncogenic markers, including pAkt(S473), pSTAT3 (Y705 & S727), β-catenin, Cyclin D1, Mc1-1, HER2, EGFR, VEGFR2, c-Myc, CD44, and Oct-4 in pancreatic cancer cells. Further studies revealed that Pimavanserin inhibits glycolysis and mitochondrial respiration in pancreatic cancer cells. Further, Western blot analysis shows that Pimavanserin inhibits the expression of main metabolic markers, including Hexokinase-1, LDH-A and FOXM1, while also increasing the cleavage of caspase3 and PARP. These showing an apoptosis-inducing effect.

Pimavanserin is listed under the trade name NUPLAZID® and is sold to treat hallucinations and delusions due to Parkinson's disease psychosis, and its listed and observed side effects are minimal to non-existent. In the disclosed technology, 10 mg/kg of Pimavanserin was administered to mice every day for 65 days. This dosage led to 75% suppression in tumor growth in an orthotopic pancreatic cancer model.

Isolated or purified Pimavanserin has been separated from its environment during manufacture, such as from a crude reaction mixture if made in a laboratory setting or removed from their natural environment (if naturally occurring). Examples of the purity of the isolated compound include, for example, at least 50%, 55%, 60%, 65%, 70%, 75%, 80%, 85%, 90%, 95%, 96%, 97%, 98%, 99%, to 100% by weight.

Another aspect of the invention provides a unit quantum of a compound described herein, such as an amount of at least (a) one microgram of a disclosed compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

Doses of a compound provided herein, or a pharmaceutically acceptable salt thereof, vary depending on factors such as: specific indication to be treated; age and condition of a patient; and amount of a second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 0.1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, Pimavanserin is administered at a daily dosage in the range of about 25 mg to 50 mg, 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, Pimavanserin is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, Pimavanserin is administered at a daily dosage in the range of about 25 mg to 50 mg, 50 mg to 75 mg, 75 mg to 100 mg, 100 mg to 125 mg, 125 mg to 150 mg or 150 mg to 175 mg. In certain embodiments, Pimavanserin is administered at a daily dosage in the range of about 125 mg to 175 mg. In certain embodiments, Pimavanserin is administered at a daily dosage in the range of about 140 mg to 160 mg. In yet other embodiments, Pimavanserin is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Adikrisna R, Tanaka S, Muramatsu S, Aihara A, Ban D, Ochiai T, et al. Identification of pancreatic cancer stem cells and selective toxicity of chemotherapeutic agents. Gastroenterology. 2012; 143(1):234-45 e7.
2. Onishi H, Katano M. Hedgehog signaling pathway as a new therapeutic target in pancreatic cancer. World journal of gastroenterology. 2014; 20(9):2335-42.
3. Subramani R, Gonzalez E, Nandy S B, Arumugam A, Camacho F, Medel J, et al. Gedunin inhibits pancreatic cancer by altering sonic hedgehog signaling pathway. Oncotarget. 2017; 8(7):10891-904.
4. Kasai K. GLI1, a master regulator of the hallmark of pancreatic cancer. Pathology international. 2016; 66(12): 653-60.
5. Marechal R, Bachet J B, Calomme A, Demetter P, Delpero J R, Svrcek M, et al. Sonic hedgehog and Gli1 expression predict outcome in resected pancreatic adenocarcinoma. Clinical cancer research: an official journal of the American Association for Cancer Research. 2015; 21(5):1215-24.
6. Inaguma S, Riku M, Hashimoto M, Murakami H, Saga S, Ikeda H, et al. GLI1 interferes with the DNA mismatch repair system in pancreatic cancer through BHLHE41-mediated suppression of MLH1. Cancer research. 2013; 73(24):7313-23.
7. Ranjan A, Srivastava S K. Penfluridol suppresses glioblastoma tumor growth by Akt-mediated inhibition of GLI1. Oncotarget. 2017; 8(20):32960-76.
8. Wiklund E D, Catts V S, Catts S V, Ng T F, Whitaker N J, Brown A J, et al. Cytotoxic effects of antipsychotic drugs implicate cholesterol homeostasis as a novel chemotherapeutic target. International journal of cancer. 2010; 126(1):28-40.
9. Ranjan A, German N, Mikelis C, Srivenugopal K, Srivastava S K. Penfluridol induces endoplasmic reticulum stress leading to autophagy in pancreatic cancer. Tumour biology: the journal of the International Society for Oncodevelopmental Biology and Medicine. 2017; 39(6): 1010428317705517.
10. Ranjan A, Wright S, Srivastava S K. Immune consequences of penfluridol treatment associated with inhibition of glioblastoma tumor growth. Oncotarget. 2017; 8(29):47632-41.
11. Ranjan A, Srivastava S K. Penfluridol suppresses pancreatic tumor growth by autophagy-mediated apoptosis. Scientific reports. 2016; 6:26165.
12. Ranjan A, Gupta P, Srivastava S K. Penfluridol: An Antipsychotic Agent Suppresses Metastatic Tumor Growth in Triple-Negative Breast Cancer by Inhibiting Integrin Signaling Axis. Cancer research. 2016; 76(4): 877-90.
13. Yuan K, Yong S, Xu F, Zhou T, McDonald J M, Chen Y. Calmodulin antagonists promote TRA-8 therapy of resistant pancreatic cancer. Oncotarget. 2015; 6(28):25308-19.
14. Sonier B, Arseneault M, Lavigne C, Ouellette R J, Vaillancourt C. The 5-HT2A serotoninergic receptor is expressed in the MCF-7 human breast cancer cell line and reveals a mitogenic effect of serotonin. Biochemical and biophysical research communications. 2006; 343(4): 1053-9.
15. Gooz M, Gooz P, Luttrell L M, Raymond J R. 5-HT2A receptor induces ERK phosphorylation and proliferation through ADAM-17 tumor necrosis factor-alpha-converting enzyme (TACE) activation and heparin-bound epidermal growth factor-like growth factor (HB-EGF) shedding in mesangial cells. The Journal of biological chemistry. 2006; 281(30):21004-12.
16. Srivastava S K, Singh S V. Cell cycle arrest, apoptosis induction and inhibition of nuclear factor kappa B activation in anti-proliferative activity of benzyl isothiocyanate against human pancreatic cancer cells. Carcinogenesis. 2004; 25(9):1701-9.

The invention claimed is:

1. A method of treating a cancer comprising administering to a subject a pharmaceutical composition comprising Pimavanserin in an amount sufficient to treat the cancer in the subject and a pharmaceutically acceptable carrier, wherein the cancer is a pancreatic cancer, a colon cancer, a breast cancer, or a melanoma, wherein the step of administering results in at least one of the following: a 10% reduction in size of tumors, at least a 10% reduction in number of cancer metastases, at least a 10% increase in activity of immune system against the cancer cells, or at least a 10% improvement in clinical signs and symptoms related to cancer.

2. The method of claim 1, wherein the breast cancer is a triple negative breast cancer, is a metastatic cancer, is a high microsatellite instability-high (MSI-high) cancer, or the cancer is under normoxic or hypoxic conditions.

3. The method of claim 1, wherein the Pimavanserin has no side effects.

4. The method of claim 1, wherein the Pimavanserin is adapted for oral, enteral, parenteral, intravenous, pulmonary, nasal, or rectal administration.

5. The method of claim 1, wherein the Pimavanserin is provided in the form of a salt selected from at least one of a phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, tartrate or naphthalenesulfonate.

6. The method of claim 1, further comprising providing one or more chemotherapeutic agents, wherein the Pimavanserin enhances that activity of the one or more chemotherapeutic agents, or one or more immunotherapeutic agents, wherein the Pimavanserin enhances that activity of the one or more immunotherapeutic agent.

7. A method of treating a pancreatic, skin, colon, or breast cancer, comprising administering to a subject a pharmaceutical composition comprising Pimavanserin, or salts thereof in an amount sufficient to treat the reproductive cancer in the subject and a pharmaceutically acceptable carrier.

8. A method treating a cancer in a patient, the method comprising:
- administering the Pimavanserin to a first subset of cancer cells obtained from the patient, and a placebo to a second subset of cancer cells;
- determining if the Pimavanserin reduces the number of cancer cells that is statistically significant as compared to any reduction occurring in the second subset of cancer cells, wherein a statistically significant reduction indicates that the Pimavanserin is useful in treating that cancer; and
- treating the patient with the Pimavanserin and, wherein the cancer is a pancreatic cancer, a colon cancer, a breast cancer, or a melanoma.

9. The method of claim 8, further comprising the step of modifying formulation to the route of delivery to enhance the activity of the Pimavanserin against the cancer.

* * * * *